United States Patent [19]

Klodowski

[11] Patent Number: 5,071,768

[45] Date of Patent: * Dec. 10, 1991

[54] METHOD AND APPARATUS FOR REFRIGERANT TESTING IN A CLOSED SYSTEM

[75] Inventor: Harry F. Klodowski, East Syracuse, N.Y.

[73] Assignee: Carrier Corporation, Syracuse, N.Y.

[*] Notice: The portion of the term of this patent subsequent to May 8, 2007 has been disclaimed.

[21] Appl. No.: 449,679

[22] Filed: Dec. 12, 1989

Related U.S. Application Data

[63] Continuation-in-part of Ser. No. 32,106, Mar. 14, 1987, Pat. No. 4,923,806, which is a continuation-in-part of Ser. No. 746,491, Jun. 14, 1985, abandoned.

[51] Int. Cl.⁵ ...................... G01N 31/22; G01N 33/18
[52] U.S. Cl. .......................................... 436/39; 62/127; 62/128; 62/129; 422/60; 422/86; 422/88; 422/104; 436/41; 436/100; 436/129; 436/136; 436/144; 436/167
[58] Field of Search ................... 436/39, 41, 100, 129, 436/136, 144, 167; 422/60, 86, 88, 104; 62/125, 127-129

[56] References Cited

U.S. PATENT DOCUMENTS

| 2,429,694 | 10/1947 | King ........................................ 436/39 |
| 3,127,249 | 3/1964 | Carroll ..................................... 422/86 |
| 3,539,302 | 11/1970 | Dreckmann ...................... 436/122 X |
| 3,625,656 | 12/1971 | Paulson .................................... 422/86 |
| 4,018,061 | 4/1977 | Williamitis ............................. 62/125 |
| 4,022,578 | 5/1977 | Kretschner . |
| 4,259,287 | 3/1981 | Leichnnitz ......................... 422/60 X |
| 4,271,125 | 6/1981 | Leichnitz ........................... 422/60 X |
| 4,300,910 | 11/1981 | Pannwitz ........................... 422/60 X |
| 4,329,153 | 5/1982 | Leichnitz ........................... 422/60 X |
| 4,330,297 | 6/1983 | Leichnitz ........................... 422/60 X |
| 4,389,372 | 6/1983 | Lalin ..................................... 422/88 |
| 4,460,544 | 7/1984 | Leichnitz ........................... 422/60 X |
| 4,866,994 | 9/1989 | Baker ..................................... 62/125 |
| 4,923,806 | 5/1990 | Klodowski ...................... 422/104 X |

Primary Examiner—Jill Johnston

[57] ABSTRACT

A method and apparatus for testing for the presence and concentration of contaminants in a refrigerant. A sample of the refrigerant is withdrawn from a closed refrigeration, air conditioning or similar system and passed through a testing tube. Various sections of the tube contain provisions for the removal of oil entrained in the sample, for the removal of water contamination from the sample and for providing visual indications of the presence and concentration of a plurality of contaminants that may be present in the refrigerant.

21 Claims, 6 Drawing Sheets

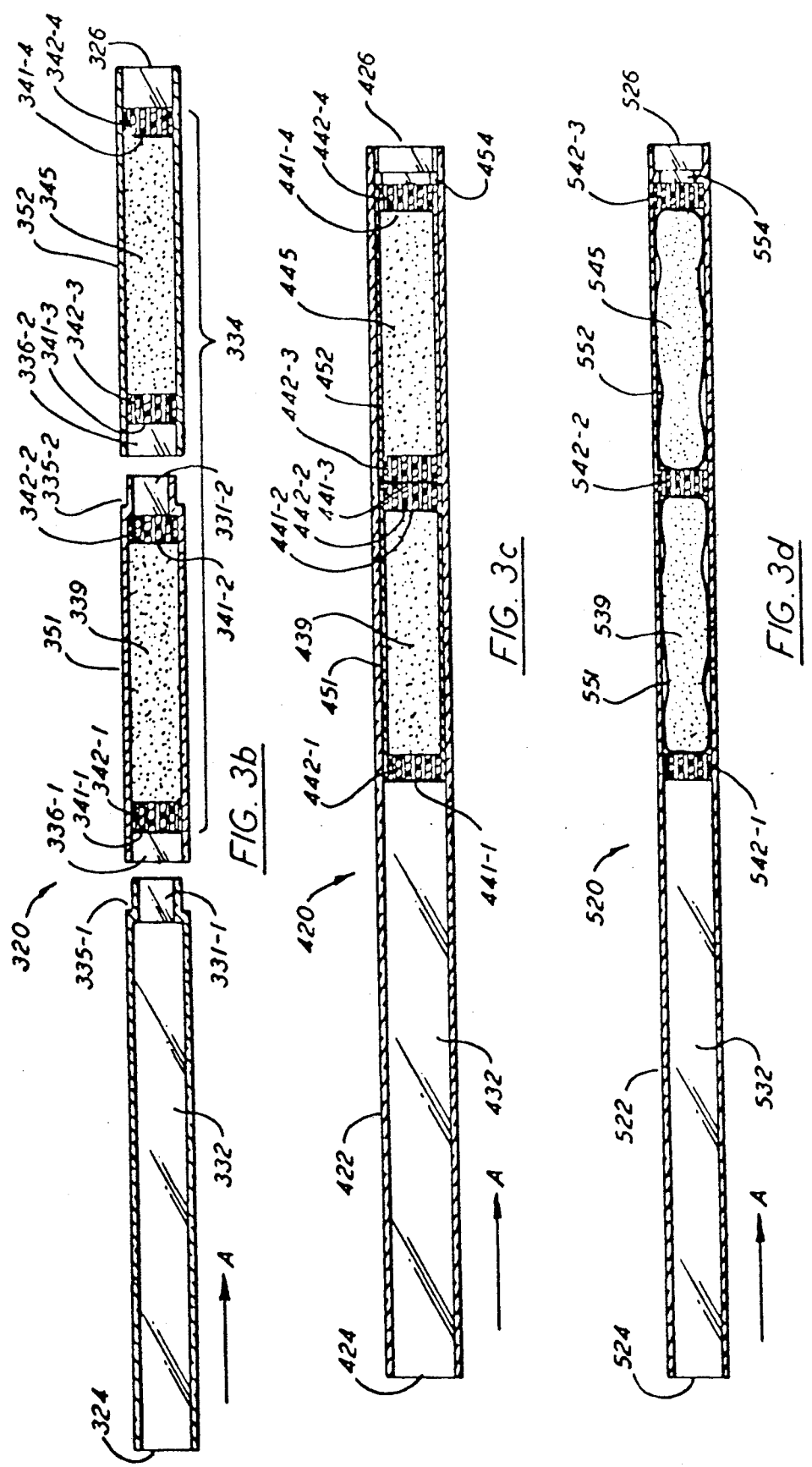

METHOD AND APPARATUS FOR REFRIGERANT TESTING IN A CLOSED SYSTEM

This application is a continuation-in-part of application Ser. No. 032,106 which was filed on March 14, 1987, now U.S. Pat. No. 4,923,806, which application is in turn a continuation-in-part of application Ser. No. 746,491 which was filed on June 14, 1985 and is now abandoned.

BACKGROUND OF THE INVENTION

A number of fluorocarbon compounds and azeotropes are commonly used as refrigerants in various types of air conditioning and refrigeration systems. These refrigerants have different properties such as boiling point and vapor pressure that dictate to a great extent a given refrigerant's suitability for a particular application. Refrigeration systems are generally classified as either high pressure systems or low pressure systems depending on the system operating pressure. The refrigerants used in these systems are therefore commonly referred to as either high pressure or low pressure refrigerants depending upon the operating pressure of the system in which they are used. The vapor pressure of a given refrigerant at normal ambient temperatures can range from 140 kPa for a low pressure refrigerant to over 1400 kPa for a high pressure refrigerant.

In many such systems, a small amount of lubricating oil is added to and circulates with the refrigerant. Both refrigerants and lubricating oils tend to absorb and hold water. Any water introduced into an air conditioning or refrigeration system will therefore be captured by and circulate with the refrigerant and oil. Excessive water within the system can cause ice to form, promote corrosion of metal components of the system, damage motor insulation in hermetic compressors or damage other system components. Water can be present in a refrigeration or air conditioning system due to improper drying of equipment during manufacture or servicing, leaks in the system, wet refrigerant, water contaminated oil, oxidation of hydrocarbons in the oil and decomposition of cellulose insulation in hermetically sealed units. To assure efficient system operation and prevent damage, it is necessary to detect the presence of water contamination and remove it from the system.

Acid contamination can also be present in a refrigeration or air conditioning system due to chemical breakdown of the refrigerant caused by overheating in the compressor. The principal acid contaminant due to refrigerant breakdown is hydrochloric acid. Other acids can be produced as the decomposition products of oil, insulation, varnish, gaskets and adhesives. Like water, some of these acids can be carried through the system with the refrigerant and build up to levels which can be indicative of the failure or potential failure of system components.

Oxygen and carbon dioxide can also be present in a refrigeration or air conditioning system as a result of incomplete system evacuation before refrigerant fill or low side in-leakage. In addition, carbon dioxide can be present due to the overheating and resultant decomposition of organic insulation materials such as may occur in a motor burnout. Carbon monoxide can also be formed as a result of overheated insulation. Hydrogen may be present as a result of bearing wear. Excessive concentrations of these noncondensable gases in the system can reduce system efficiency, but their presence is also evidence of the cause of defective or inoperative system components.

To correct a refrigerant contamination problem, it is necessary to identify the contaminants present. Identification of contaminants can also aid in troubleshooting defective or inoperative refrigeration or air conditioning systems. Prior art testing procedures for water contamination in a closed system have usually required removal of all the refrigerant from the system. The presence of acids and other contaminants have usually been determined by separate tests conducted on the system lubricating oil.

SUMMARY OF THE INVENTION

The present invention is directed to a method and apparatus for quantitatively testing refrigerants in closed refrigeration, air conditioning or similar systems, such as refrigerant recovery and reclamation equipment, for the presence of a number of refrigerant contaminants in a single test without withdrawing more refrigerant than is needed for the test. The test produces valid indications whether the contaminants are in a liquid or vapor state, whether or not the system is operating and is adaptable for use in both high and low pressure systems.

It is an object of this invention to provide a method and apparatus for detecting liquid and gaseous contaminants in the refrigerant in a closed air conditioning or refrigeration system without removing all of the refrigerant charge from the system.

It is another object of this invention to remove oil from the refrigerant in the detecting apparatus before the refrigerant contacts the indicating media.

It is an additional object of this invention to provide a method and apparatus for testing a system having a hermetically sealed compressor, whether the compressor has failed or is operating, without disassembly, to determine the mode of compressor failure or the condition of the system.

It is another object of this invention to determine the presence of acids in refrigerants.

It is another object of this invention to determine the presence of contaminants in the refrigerant in a hermetically sealed compressor without removing the refrigerant charge from the system.

It is a further object of this invention to provide a single test for the presence of a number of other contaminants in a refrigerant, including volatile organic acids, oxygen, carbon dioxide, carbon monoxide and hydrogen.

These objects, and others, are accomplished by the present invention.

The present invention provides a method and apparatus for testing a refrigerant contained in a closed system for the presence and concentration of contaminants in a single testing operation. The method is capable of testing for water, inorganic acids, volatile organic acids, oxygen, carbon dioxide, carbon monoxide and hydrogen or for any one or combination of contaminants taken from that group. In a test for a contaminant, a continuous small sample flow of refrigerant is withdrawn from the system and directed through a testing tube. The testing tube contains a demister section to separate any oil that is entrained in the refrigerant, a water removal section and one or more contaminant indicating sections. The water removal section may also indicate the presence and concentration of water contamination. The apparatus includes means for reducing, if necessary, system pressure to a pressure near ambient before the sample flow enters the tube. The apparatus also includes a means for directing all of the sample flow through the tube and may include a testing tube holder that provides support and protection for the tube and, as well, means for providing indication of sample flow. The testing tube and other components of the apparatus are prepared for a test by placing them in flow communication with the system to be tested, with the pressure reducing means between the system and the tube. Means for isolating the removal and indicating media from the environment external to the testing tube are removed from the tube before the test is commenced and/or by breaching at the commencement of the test. The test is conducted by directing refrigerant sample flow through the testing tube and the separating, removal and indicating sections of the tube for a predetermined time. The presence of a given contaminant is indicated by a color change in an appropriate indicating medium in the testing tube and the concentration is determined by comparison of the changed color of the medium to a color chart and/or the extent of propagation of the color change through the medium.

BRIEF DESCRIPTION OF THE DRAWINGS

The accompanying drawings form a part of the specification. Throughout the drawings, like reference numbers designate like or corresponding elements.

FIGS. 3b through 3e are cross sectional views of additional alternate embodiments of the contaminant testing tube depicted in FIG. 2.

DESCRIPTION OF THE PREFERRED EMBODIMENTS

Figure 1:
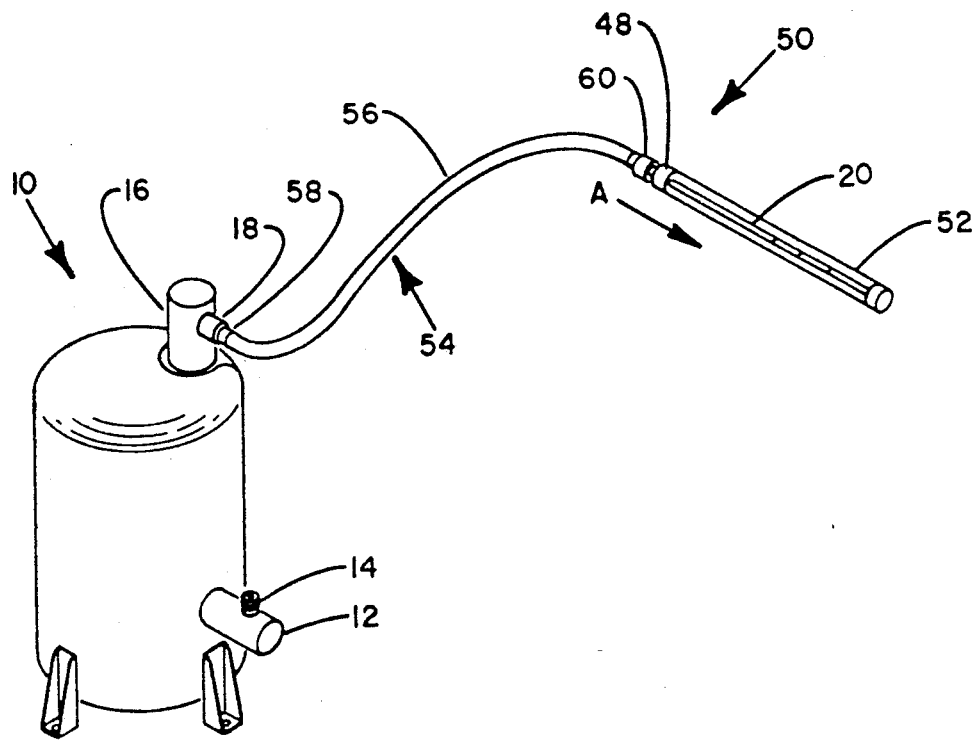
FIG. 1 is a perspective view of a preferred embodiment of the present invention in use with a portion of a refrigeration, air conditioning or similar system.

FIG. 1 depicts the present invention being used in conjunction with a compressor 10 of a refrigeration, air conditioning, or similar closed system incorporating a compressor. Compressor 10 has a suction line 12 containing service valve 14 and a discharge line 16 containing service valve 18. The figure illustrates the invention in use to test for the presence of contaminants in the refrigerant leaving compressor 10 via discharge line 16. The present invention may be used to sample the refrigerant at other points in the system such as suction line 12. The present invention can be used to test refrigerants in both high and low pressure systems. Moreover, the present invention can be used to test for contaminants in other types of systems. In FIG. 1, as well as in FIGS. 2 through 4, arrow A denotes the direction of refrigerant sample flow during a test.

Figure 2:
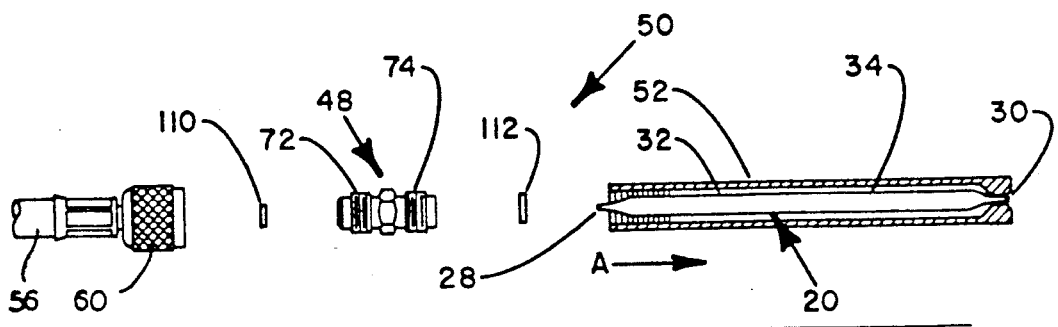
FIG. 2 is an exploded view of a contaminant testing tube holder apparatus and a contaminant testing tube of the embodiment depicted in FIG. 1.
Figure 3:
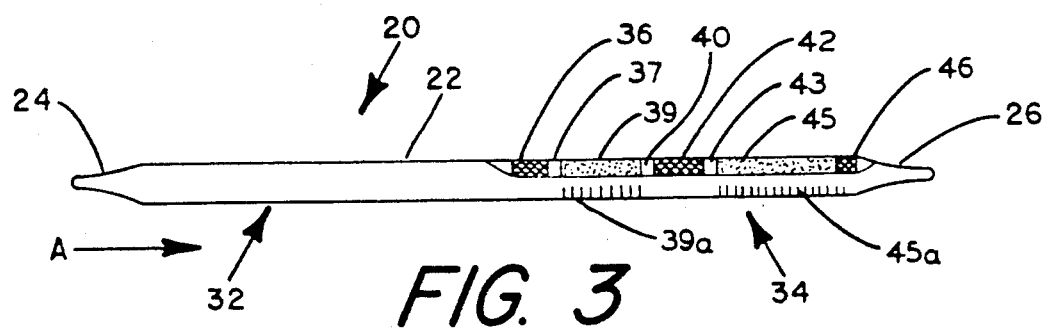
FIG. 3 is a partially cut away side elevational view of the contaminant testing tube depicted in FIG. 2.

FIG. 3 depicts a contaminant testing tube 20 for detecting the presence of water and inorganic acid contaminants in a refrigerant according to one embodiment of the invention. Testing tube 20 is a generally cylindrical tube 22 made of a suitable transparent material such as glass. Tube 22 has two oppositely disposed tapered ends terminating respectively in frangible inlet tip 24 and frangible outlet tip 26. Tips 24 and 26 are intended to be broken off just prior to use thus forming open inlet end 28 and open outlet end 30 (FIG. 2). Testing tube 20 is divided into demister section 32, for oil separation, and contaminant indicating section 34. In one embodiment, tube 22 is 130 mm in overall length and 105 mm in length excluding the tapers at the tips. In the same embodiment, the inside and outside diameters of tube 22 are 4 mm and 6 mm respectively. In the assembled tube 20, demister section 32 extends from inlet end 24 for about half the length of tube 22. Its function is to separate entrained oil from the refrigerant before the refrigerant reaches contaminant indicating section 34 as will be fully described below.

From the inlet end of contaminant indicating section 34 and proceeding in the direction of sample flow (arrow A), tube 22 contains a 3 mm length of brass screen 36, a 1 mm thick glass fiber disk 37, a 12 mm long water removal and indicator section 39, a 1 mm thick glass fiber disk 40, an 8 mm length of rolled brass screen 42, a 1 mm thick glass fiber disk 43, a 25 mm long acid indicator section 45 and a 3 mm length of brass screen 46. The chemical indicator media contained in water removal and indicator section 39 and in acid indicator section 45 are located in tube 22 relative to markings 39a and 45a, respectively, or markings 39a and 45a are placed on tube 22 after tube 22 is sealed. In addition to glass fiber, partitioning disks 37, 40 and 43 can be made of other material such as a suitable metal or plastic. Partitioning disks 37, 40 and 43 primarily serve as wadding to keep the chemical indicating media in place as well as to provide physical separation and prevent cross contamination between the indicating media. The number and configuration of the disks is dependent upon the number and type of indicating media they separate, the dimensions of tube 22 and the like. The primary function of screen or filter members 36, 42 and 46 is to contain the indicating media within indicating sections 39 and 45 and disks 37, 40 and 43 in place in contaminant indicating section 34 as well as providing, in the case of screen 42, physical separation for the chemicals. Screen or filter members 36, 42 and 46 screen or filter out particulate matter, but do not absorb any contaminants to be detected in indicator sections 39 and 45. Should the screen, filter members or disks absorb any of the contaminants to be detected, indicator sections 39 and 45 could produce inaccurate indications of the concentrations of contaminants present in the refrigerant. Screen or filter members 36, 42 and 46, in addition to the preferred brass, can be made of any other suitable material.

Disposed on the outer surface of contaminant indicating section 34 are a series of scale or reference markings 39a and 45a for readily determining the length of the color change in respective indicator sections 39 and 45. The distances between individual markers making up markings 39a and 45a is empirically determined based upon the type of indicating medium, the dimensions of tube 22, the granularity of the indicating medium and the like. Markings 39a and 45a can be disposed on tube 22 by means of an adhesive, etching or the like.

Alternatively, markings 39a and/or 45a can be eliminated and the contaminant concentration determined by color change of an entire indicator section 39 or 45. The concentration of contaminant(s) is then determined by the use of a color coded card. For example, matching the shade of the changed indicating medium color with the same shade on the color coded card can indicate the concentration or amount of contaminant present, with each color shade on the card representing a predetermined concentration of contaminant. The coded cards can also indicate a recommended servicing procedure for removing the given contaminant.

If they come in contact, there can be interactions between the water removal and indicating medium and the acid indicating medium resulting in color changes not representative of the presence of water or acid in the refrigerant sample. Glass fiber disk 40, rolled brass screen 42 and glass fiber disk 43 serve to separate the indicating media. The respective media can also react with moisture and other constituents of ambient air. Frangible tips 24 and 26 serve to isolate the contents of testing tube 20 from the external environment until the tips are broken off just prior to use.

As noted above, lubricating oil is usually added to the refrigerant in a refrigeration, air conditioning or similar system and circulates with the refrigerant through the system. A sample drawn from the system will therefore also contain a small amount of oil. If oil in the sample flow comes in contact with any of the indicating media, it could cause false or inaccurate indications of the presence of a contaminant. It is therefore desirable to separate any entrained oil from the refrigerant sample flow.

Referring to FIGS. 2 and 3, separation of entrained oil from the refrigerant is accomplished by means of demister section 32 of testing tube 20 acting in conjunction with flow restrictor 48. The pressure of the refrigerant sample is reduced from system pressure to a pressure near ambient as the refrigerant passes through restrictor 48 and before it enters testing tube 20 through open inlet end 28. Because of the pressure decrease, entrained oil vapors separate from the refrigerant and collect on the side of demister section 32 as minute droplets. The length of demister section 32 can vary depending upon the system pressure, the dimensions of tube 22, the anticipated amount of oil entrained in the vapor and the like.

FIGS. 1 and 2 depict contaminant testing tube holder apparatus 50 containing testing tube 20. Testing tube holder apparatus 50 comprises tube container 52, flow restrictor 48 and fluid hose 54, which may be a standard refrigerant hose. Fluid hose 54 includes hose line 56 having on one end connector 58, typically a Schraeder type fitting, for connection to service valve 18 and connector 60 at the other end for connecting to flow restrictor 48.

Figure 4:
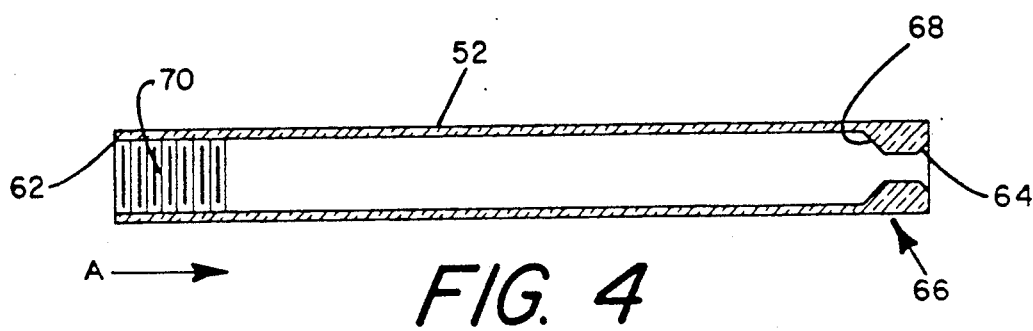
FIG. 4 is a longitudinal sectional view of a tube container in the contaminant testing tube holder apparatus depicted in FIG. 2.

Tube container 52, depicted in FIG. 4, is made of a suitable transparent material, such as a polycarbonate or acrylic plastic, and has an inside diameter sized to contain testing tube 20, as illustrated in FIGS. 1 and 2. Tube container 52 includes oppositely disposed open inlet end 62 and open outlet end 64. Support member 66, located at open outlet end 64, includes continuous beveled surface 68 sloping radially inward and axially outward for centrally supporting conical open inlet end 30 of testing tube 20. Other means of support can be used to centrally locate open outlet end 30 in tube container 52. Open inlet end 62 has an internally threaded surface portion 70 for connection to flow restrictor 48.

Figure 5:
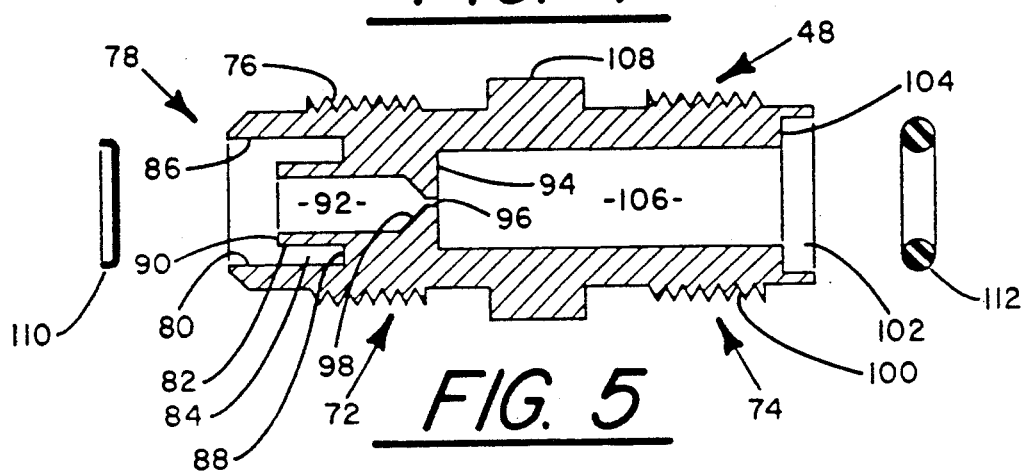
FIG. 5 is an enlarged and exploded view in cross section of the flow restrictor in the contaminant testing tube holder apparatus in depicted FIG. 2.

FIG. 5 depicts flow restrictor 48, an elongated body having oppositely disposed end sections 72 and 74. End section 72 includes a threaded surface 76 for attaching flow restrictor 48 to connector 60 of fluid hose 54 and pressure reducing means 78 disposed just inward of opening 80. Pressure reducing means 78 includes collar section 82 spaced axially and radially inward of opening 80 to define annular space 84 between inner surface 86 and the outer surface of collar section 82. Collar section 82 also defines annular bottom surface 88, annular remote end surface 90 and passage 92. Pressure reducing means 78 further comprises wall member 94 at the innermost end of passage 92 within which is disposed small orifice 96. In this embodiment, the diameter of orifice 96 is sized to provide a refrigerant vapor flow of about 300 cc/min when operating at a refrigerant pressure of about 900 kPa. Within passage 92 is continuous beveled surface 98 sloping radially inward and axially inward towards wall member 94 and defining the entrance to orifice 96. Pressure reducing means 78 can be configured to produce greater or lesser flows or to produce the same flow at higher or lower refrigerant pressures.

End section 74 includes externally threaded surface 100 for attaching flow restrictor 48 to threaded surface portion 70 of tube container 52. End section 74 further includes opening 102, annular groove 104 and passage 106 in fluid communication with passage 92 through orifice 96. The outer surface of end section 74 also includes hex nut flange 108 to assist in manually connecting flow restrictor 48 to fluid hose 54 and tube container 52. As illustrated, passage 106 is larger in diameter than passage 92.

A vapor permeable screen or filter 110 is disposed in opening 80 of end section 72 and rests against annular remote end surface 90 of collar section 82. On the opposite end of flow restrictor 48, a seal, such as O-ring 112, is fitted in annular groove 104 to provide a fluid tight fit between flow restrictor 48 and open inlet end 28 of testing tube 20 so that all of the refrigerant sample flow passes through tube 20. Screen or filter 110 filters particulate matter out of the refrigerant sample flow not intended to be detected in indicator sections 39 and 45 of testing tube 20 and prevents clogging of orifice 96.

Alternatively, flow restrictor 48 or pressure reducing means 78 could be disposed in connector 58 of hose line 56 to provide the desired refrigerant sample flow rate through line 56 and tube 20 or pressure reducing means 78 can be disposed at open inlet end 64 of tube container 52.

Figure 7:
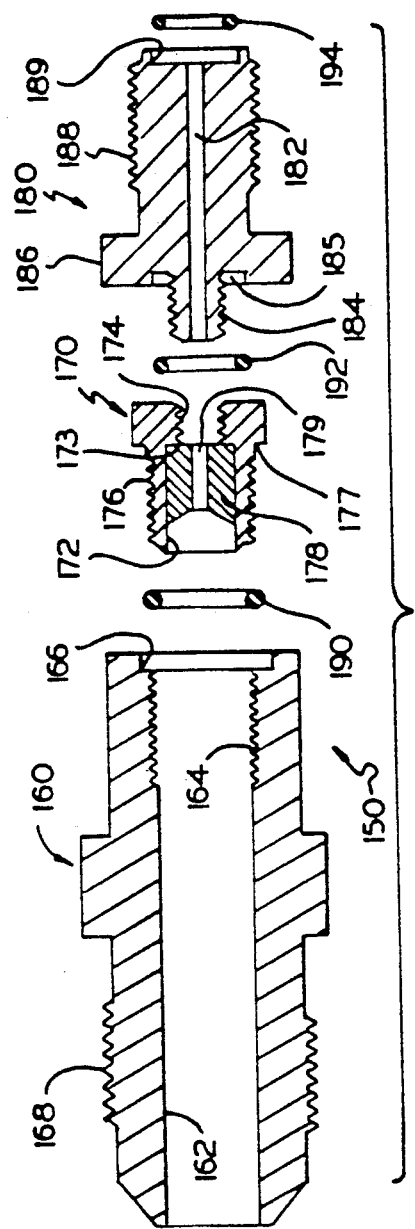
FIG. 7 is an exploded cross sectional view of a modified flow restrictor.

FIG. 7 depicts a modified flow restrictor 150 which may be used in place of flow restrictor 48 (FIG. 5). Flow restrictor assembly 150 includes orifice holder 160, retainer 170, cap 180 and O-rings 190, 192 and 194. Orifice holder 160 has bore 162 which includes threaded section 164 terminating in annular relieved portion 166. Threads 168 are formed on the exterior of orifice holder 160 and correspond to threads 76 of flow restrictor 48 (FIG. 5). Threads 168 serve to permit connection of orifice holder 160 to connector 60. Orifice retainer 170 has first bore 172 and threaded second bore 174 with shoulder 173 between the two bores. Threaded portion 176 is formed on the exterior of orifice retainer 170 and terminates at shoulder 177.

Threaded section 164 and threaded portion 176 can be threaded together so as to force O-ring 190 into relieved portion 166 to form a seal between orifice holder 160 and orifice retainer 170. Orifice 178, containing passage 179, is pressed into bore 172. Passage 179 can be selected to provide a desired flow rate. Cap 180 has bore 182 extending through it together with first threaded portion 184, second threaded portion 188 and hex nut flange 186 with annular recess 185. Second annular recess 189 is formed in the downstream end of hex nut flange 186. First threaded portion 184 is received in threaded second bore 174 and forces O-ring 192 into recess 185 to form a seal between orifice retainer 170 and cap 180. Second threaded portion 188 corresponds to externally threaded surface 100 and is engagable with threaded surface portion 70 of tube container 52. O-ring 194, in conjunction with recess 189 and conically shaped upstream open end 28 of testing tube 20, forms a seal so that all of the refrigerant flows through bore 182 into testing tube 20 (FIG. 2). A filter (not illustrated) such as screen 110 (FIG. 5) may be located at any suitable location upstream of orifice 178.

Figure 6:
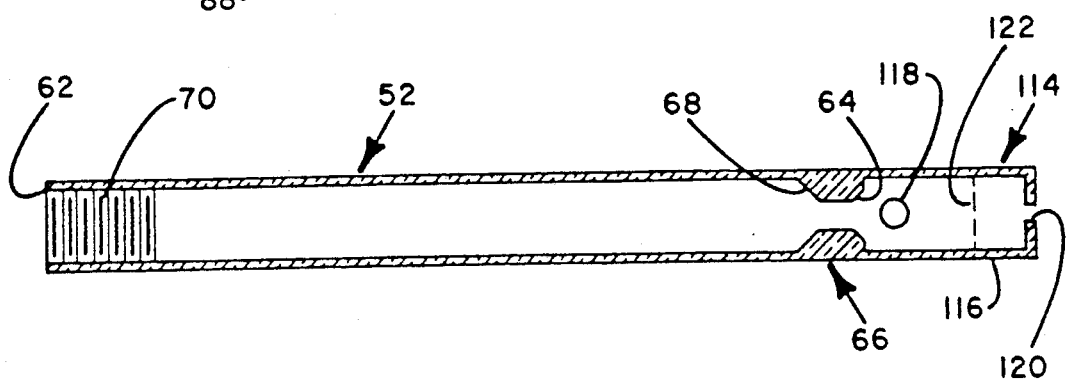
FIG. 6 is a longitudinal section view of a modified tube container.

FIG. 6 depicts tube container 52 modified to include flow indicator 114 at downstream open end 64. Flow indicator 114 indicates that a proper refrigerant sample flow rate exists to ensure accurate indication of the contaminants being tested for. Flow indicator 114 comprises chamber 116, which can be integral with tube container 52 or made separately and then attached to tube container 52 by any suitable means and an indicator element such as pith ball 118 or flow line 122 disposed in chamber 116.

In operation., after connection to compressor 10, tube container 52 is held vertically so that flow indicator 114 is above the container. If an adequate sample flow rate exists, it will cause ball 118 to be urged upwardly to flow line 122. If ball 118 does not reach line 122, then the sample flow rate is less than desirable. Inadequate sample flow rate can indicate a blockage in the system, the testing apparatus or the like.

Ball 118 has a diameter greater than that of open end 64 and opening 120 and can be made of any suitable lightweight material. Further, flow indicator 114 can be a separate device which can be used by manually holding it in place, engaging open end 64 of tube container 52 and directing all of the sample flow passing through open end 64 through the flow indicator.

Other means for indicating flow rate, such as a thin filament can be used. At a predetermined, acceptable flow rate, the filament can be designed to be parallel to the general direction of sample flow. Any nonparallel position of the filament indicates a less than desirable flow rate. Discharge opening 120 may also be configured so that it produces an audible indication (e.g., a whistling sound) that there is sample flow or so that a bladder-like device (e.g. a balloon) can be fitted over it to indicate sample flow by inflation.

FIGS. 3a through 3d depict several alternate testing tube embodiments. Each is generally similar in configuration and dimensions to testing tube 20 (FIG. 3), so as to enable any of the embodiments to be used with testing tube holder apparatus 50 (FIGS. 1,2,4, and 5). The configuration and dimensions of apparatus 50 may also be modified to accommodate a testing tube of a different size or construction. The various embodiments share several features and characteristics in common.

Figure 3A:
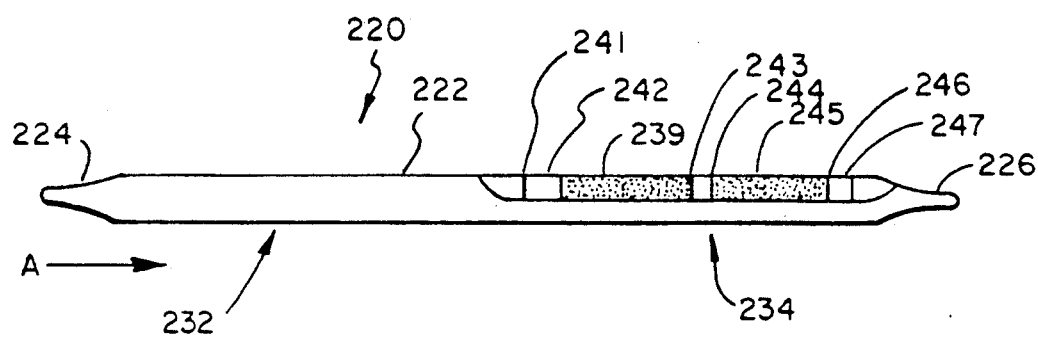
FIG. 3a is a partially cut away side elevational view of a second embodiment of the contaminant testing tube depicted in FIG. 2.

In FIG. 3a, testing tube 220 comprises tube 222 made of a suitable material, such as glass, and having frangible inlet end 224 and frangible outlet end 226, ends 224 and 226 being tapered. Testing tube 220 is divided into demister section 232 and contaminant indicating section 234. Contaminant indicating section 234 contains membrane 241, support disk 242, water indicator and removal section 239 containing an appropriate removal and indicating medium, membrane 243, support disk 244, acid indicator section 245 containing an appropriate indicating medium, membrane 246 and support disk 247.

Testing tube 320 is depicted in FIG. 3b in an exploded view as it might appear just prior to final assembly of its various sections. Tube 320 is divided into demister section 332 and contaminant indicating section 334. Contaminant indicating section 334 comprises water removal and indicator subsection 351 and acid indicator subsection 352. During final assembly of the sections, male outlet end 335-1, having passage 331-1, of demister section 332 is fitted to female inlet end 336-1 of water indicator and removal subsection 351 and similarly, male outlet end 335-2, having passage 331-2, of water indicator and removal subsection 351 is fitted to female inlet end 336-2 of acid indicator subsection 352, thus forming a single tubular member. Section 332 and subsections 351 and 352 may be slideably fitted and fixed together by suitable adhesive, chemical welding or other means. The section ends may also be suitably threaded and joined in that manner. Disk 342-4 may be prevented from being forced out of acid indicator section 352 under the urging of the refrigerant sample flow by any suitable means such as being a press (friction) fit with section 352, being fixed by adhesive or chemical welding, or by the addition of a circumferential shoulder to section 352 similar to shoulder 454 depicted in FIG. 3c. When assembled, contaminant indicating section 334 of testing tube 320 contains membrane 341-1, support disk 342-1, water indicating and removal medium 339, membrane 341-2, support disk 342-2, membrane 341-3, support disk 342-3, acid indicating medium 345, membrane 341-4 and support disk 342-4.

Testing tube 420, depicted in FIG. 3c, comprises tube barrel 422 within which are slideably fitted tubular water removal cartridge 451 and acid indicator cartridge 452. The respective inner and outer diameters of tube barrel 422 and cartridges 451 and 452 are such that all the refrigerant entering tube 422 must pass through, and not bypass, cartridges 451 and 452. Alternatively, a suitable sealing means may be employed at the inlet end of cartridge 451 upstream of membrane 441-1. Cartridges 451 and 452 are prevented from sliding out the outlet end 426 of tube barrel 422 under the urging of the refrigerant sample flow by a suitable stopping means such as circumferential shoulder 454. The dimensions of tube barrel 422 and the placement of cartridges 451 and 452 within it are such that when assembled, demister section 432 is formed just inside inlet end 424. Water removal cartridge 451 contains an appropriate removal medium 439, membranes 441-1 and 441-2 and support disks 442-1 and 442-2. Acid indicator cartridge 452 contains an appropriate indicating medium 445, membranes 441-3 and 441-4 and support disks 442-3 and 442-4.

Testing tube 520, depicted in FIG. 3d, comprises tube barrel 522 within which are contained water indicator and removal capsule 551, containing an appropriate water indicating and removal medium 539, and acid indicator capsule 552, containing an appropriate acid indicating medium 545. Support disk 542-1 is located between inlet end 524 and water indicating and removal capsule 551, support disk 542-2 is located between capsules 551 and 552 and support disk 542-3 is located between acid indicating capsule 552 and outlet end 526. The support disks and capsules are prevented from sliding out of tube 522 through outlet end 526 under the urging of the refrigerant flow by an appropriate stopping means such as circumferential shoulder 554. The dimensions of tube 522 and the placement of capsules 551 and 552 are such that when assembled a demister section 532 is formed just inside inlet end 524. Capsules 551 and 552 completely encapsulate indicating media 539 and 545 respectively. Support disks 542-1 and 542-2 are sized and fitted in tube 522 so that all the refrigerant entering tube 522 must pass through, and cannot bypass, capsules 551 and 552.

Membranes 241, 243 and 246 (FIG. 3a), membranes 341-1, 341-2, 341-3 and 341-4 (FIG. 3b), membranes 441-1, 441-2, 441-3 and 441-4 (FIG. 3c) and capsules 551 and 552 (FIG. 3d) are gas and vapor impermeable and can be made of any suitable material such as vinylidine chloride film (e.g. Dow Saran Wrap) which will isolate the various indicating media from each other and from the external environment under static unpressurized conditions but will rupture when subjected to a relatively high differential pressure across the film. Such a differential pressure is created when sample refrigerant is first introduced into testing tube 220 (FIG. 3a) or the testing tubes in the other embodiments, i.e. testing tube 320 (FIG. 3b), 420 (FIG. 3c) or 520 (FIG. 3d). Support disks 242, 244 and 247 (FIG. 3a), support disks 342-1, 342-2, 342-3 and 342-4 (FIG. 3b), support disks 442-1, 442-2, 442-3 and 442-4 (FIG. 3c), and support disks 542-1, 542-2 and 542-3 (FIG. 3d) can be made of any suitable material, (e.g. a perforated plastic) that will provide physical support to the various membranes and yet is permeable to allow a refrigerant sample flow when the membranes rupture. The sand bases, described below, of the removal and indicating media contained in capsules 551 and 552, (FIG. 3d) have the necessary physical characteristics to allow the portion of the film comprising the upstream ends of the capsules to rupture when subjected to the differential pressure resulting from the introduction of refrigerant into testing tube 520. The various testing tube embodiments may contain other means to burst or pierce the various isolation membranes at the commencement of a test.

Testing tube 220 (FIG. 3a) has two means to isolate the indicating media from the external environment before commencement of a test: membranes 241 and 246 as well as frangible ends 224 and 226. The testing tubes of the embodiments depicted in FIGS. 3b through 3c rely solely on the outermost membranes, e.g. membranes 441-1 and 441-4 (FIG. 3c) to isolate the indicating media from the external environment. The film encapsulation depicted in FIG. 3d isolate the indicating media from the external environment as well as from each other.

All of the testing tubes depicted in FIGS. 3a through 3d can have their respective tubular members made of glass, but a suitable transparent, rigid plastic such as cellulose butyrate, is more appropriate for making the tubular members of the embodiments depicted in FIGS. 3b through 3d. If the tubular members are made of plastic, then the need for the protection of tube container 52 is obviated. Then tube container 52 can be eliminated from testing tube apparatus 50, the inlet ends, e.g. end 324 (FIG. 3b) of the testing tubes can be configured so as to attach directly to flow restrictor 48 (FIGS. 2 and 5) or modified flow restrictor 150 (FIG. 7) and, if desired, the outlet ends, e.g. end 326 (FIG. 3b) of the testing tubes can be configured to contain a sample flow indicator device. These features are discussed in detail in the description of testing tube 620 (FIG. 3e) below.

The testing tube embodiments depicted in FIG. 3a through 3e may have markings disposed on the outer surfaces of their contaminant indicating sections in the same manner that markings 39a and 45a are disposed on testing tube 20 (FIG. 3).

Figure 3E:
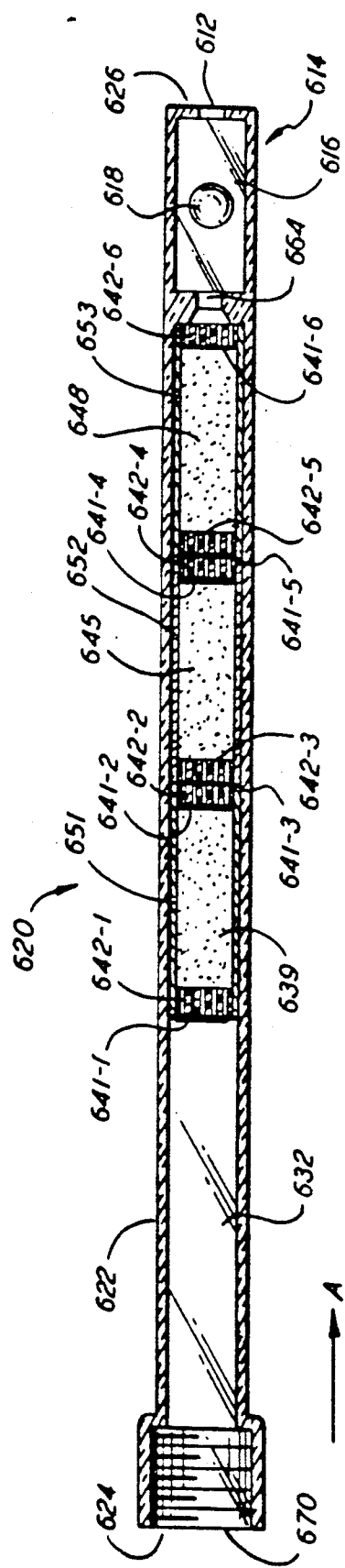

The above discussions of the various embodiments of the testing tube of the invention have, for simplicity and clarity, described tubes containing only two contaminant removal and/or indicating sections, one for the removal as well as indication of water and one for the indication of acid. In addition, the present invention encompasses other features. The testing tube depicted in FIG. 3e illustrates several of these additional features.

The testing tubes may be configured to have one or more indicator sections in addition to or in place of the indicator sections described above so that the apparatus can test for the presence of other refrigerant contaminants, including volatile organic acids, carbon dioxide, carbon monoxide, hydrogen and oxygen, thus providing a full range of tests to assist in analyzing the condition of both the refrigerant and the entire system. Testing tube 620 (FIG. 3e) is such a tube. Testing tube 620 is similar in design and construction to testing tube 420 (FIG. 3c), having tubular contaminant removal and/or indicator cartridges slideably fitted into a tube barrel, but testing tube 620 contains an additional indicator cartridge for testing a refrigerant sample for another contaminant. Testing tube 620 has other components that allow its connection directly to flow restrictor 48 (FIGS. 2 and 5) or modified flow restrictor 150 (FIG. 7) and that provide indication of refrigerant sample flow, thus eliminating the need for the use of tube holder 52 (FIGS. 2 and 4) or modified tube holder 52 with flow indicator 114 (FIG. 6).

Describing testing tube 620 in detail, it comprises tube barrel 622 having threaded inlet portion 670 at its open inlet end 624 for attaching testing tube 620 directly to flow restrictor 48 (FIGS. 2 and 5) or modified flow restrictor 150 (FIG. 7). Slideably fitted within tube barrel 622 are a plurality of cartridges 651, 652 and 653, containing contaminant removal and/or indicating media 639, 645 and 648 respectively. As with testing tube 420 (FIG. 3c), the respective inner and outer diameters of tube barrel 622 and cartridges 651, 652 and 653 are such that all the refrigerant entering tube barrel 622 must pass through cartridges 651, 652 and 653; and the dimensions of tube barrel 622 and the placement of the cartridges within it are such that, when assembled, demister section 632 is formed upstream of the cartridges. The tubular members of testing tube 620 can be made of a suitable rigid, transparent plastic. Media 639, 645 and 648 may be selected to provide for the removal of water from the refrigerant sample, the indication the presence of water in the sample, or both, as well as the indication of any of a number of other contaminants that may be present in the sample. As explained below, cartridge 651 should contain a medium that at least removes water from the sample flow, with the other cartridges and media being selected on the basis of the specific contaminants for which the testing tube will be used to test. Testing tube 620 is adaptable to factory assembly in a configuration having any number of cartridges to remove water and test for any number and combination of contaminants. The tube is also adaptable to assembly in the field by supplying tube barrel 622 and a selection of cartridges containing a selection of media. A test technician can then make an on-site determination of the specific contaminants for which to test and assemble a testing tube that contains only those cartridges that contain media appropriate to the desired test. The construction of individual cartridges 651, 652 and 653 is similar to the construction of cartridge 451 (FIG. 3c), each having gas and vapor impermeable isolation membranes, 641-1 and 641-2, 641-3 and 641-4 and 641-5 and 641-6, upstream and downstream respectively of the medium contained in each cartridge, with the membranes being supported by support disks 642-1 and 642-2 and 642-3 and 642-4 and 642-5 and 642-6 respectively. Testing tube 620 also has optional flow indicator section 614 contained within the tube just inside outlet end 626. Similar to flow indicator 114 (FIG. 6), flow indicator section 614 comprises chamber 616, passage 664 and outlet 612. Chamber 616 may contain a flow indicator element such as ball 618 to provide a visual indication of sample flow or outlet 612 may be configured to produce an audible indication of flow. Note that a testing tube similar in construction to testing tubes 220 (FIG. 3a), 320 (FIG. 3b), 420 (FIG. 3c) or 520 (FIG. 3d) could also be made with any number and combination of removal and/or indicating media in a manner similar to that described for testing tube 620. Testing tubes similar to testing tube 320 and 520 could also incorporate the features of testing tube 620 that eliminate the need for a tube holder and/or separate flow indicator. And testing tubes similar to testing tubes 320 and 520 are adaptable to field assembly in a variety of configurations.

Since most chemicals that are appropriate for use in the various indicating media are sensitive to water and thus could give false indications of the various contaminants if water is present in the refrigerant sample flow, it is advisable to include a section that at least removes water, but does not necessarily indicate its presence or concentration, in any testing tube of any configuration made or assembled according to the teaching of the present invention. This water removal section or subsection should be placed in the testing tube so that the refrigerant sample flows through it before reaching any of the other indicator sections that may be incorporated into a particular testing tube.

The water removal medium can be any suitable substance that absorbs water vapor. If the medium is also to serve as an indicator, it should also undergo a visible change (e.g. in color) in the presence of water. An excellent choice for a combined water removal and indicating medium is cobaltous chloride, as that chemical absorbs water and turns from blue to pink when exposed to moisture. A suitable cobaltous chloride medium may be prepared by applying two coats of that chemical dissolved in acetone to a sand support base. Two chloroform washes then remove any excess chemical that might later flake from the sand particles.

The acid indicating medium can be any suitable substance that undergoes a visible change in the presence of an inorganic acid having a pH of 3.2 to 4.2. A substance suitable for detecting such acids can be prepared by coating a silica sand base with a stock solution of bromophenol blue in a glycerol film. This chemical changes color from blue to yellow in the presence of such acids.

A medium suitable for indicating volatile organic acids contaminants, in the pH range of 6.2 to 7.0, can be prepared using phenol red, which undergoes a color change from pink to yellow in the presence of such acids. Such a medium can be prepared by dissolving the indicating chemical in a solvent, washing a sand base in the solution and evaporating the solvent. If both a strong and a weak (organic) acid indicator section are incorporated in the same testing tube, the weak acid indicator section should be placed downstream in the refrigerant sample flow from the strong acid indicator.

An indicating medium suitable for detecting carbon dioxide entrained in the refrigerant sample flow can be prepared from hydrazine and crystal violet, which changes color from white to violet in the presence of carbon dioxide. Such a medium can be prepared by dissolving the indicating chemical in a suitable solvent, washing a sand base in the solution and evaporating the solvent.

A medium suitable for indicating the presence of carbon monoxide can be prepared using iodine pentoxide. That compound changes color from white to black when exposed to carbon monoxide. The carbon monoxide indicating medium can be prepared by dissolving the indicating chemical in a suitable solvent, washing a sand base in the solution and evaporating the solvent.

The presence of hydrogen in the refrigerant sample flow can be indicated by a medium prepared from ammonium molybdate by dissolving that chemical in a suitable solvent, washing a sand base in the solution and evaporating the solvent. Ammonium molybdate changes from yellow to brown in color when exposed to hydrogen.

A suitable medium for indicating the presence of oxygen can be prepared from titanium tetrachloride, which changes color from black to white in the presence of oxygen. Such a medium can be prepared by dissolving the indicating chemical in a suitable solvent, washing a sand base in the solution and evaporating the solvent. If this indicating medium is used in a testing tube, it should be placed downstream of the acid indicating sections in the refrigerant sample flow, as it can emit hydrogen chloride gas which would give false acid indications in the acid indicating sections.

The below describes the procedure for testing for refrigerant contamination using the method and apparatus of the present invention employing testing tube 20 (FIG. 3).

Before conducting a test, the entire test apparatus should be purged. At a minimum, hose line 56 (FIG. 1) must be purged. Referring to FIGS. 1 and 2, the test apparatus is assembled for purging by engaging flow restrictor 48, fitted with screen 110 and O-ring 112, at threaded end section 74 to threaded surface portion 70 of tube container 52. Flow restrictor 48 is then hand tightened to tube container 52. Then threaded end section 72 of flow restrictor 48 is connected to threaded connector 60 of hose line 56. A purge flow is established by connecting hose line 56 to the system at suction line service valve 18 by means of Schraeder connector 58. Purging the test apparatus requires only a small flow of refrigerant before terminating the flow by removing Schraeder connector 58 from suction line service valve 18. Note that hose line 54 is an optional accessory that may be used for convenience in the conduct of a test. Hose line 54 may be eliminated and flow restrictor 48, provided with suitable fittings at end section 72, connected directly to suction line service valve 18.

After the test apparatus is purged and connector 58 is removed from valve 18, a testing tube 20 having the desired chemical indicating media in indicator sections 39 and 45 is prepared by breaking off frangible tips 24 and 26 to produce open ends 28 and 30. Testing tube 20 is then inserted into tube container 52 so that open outlet end 30 is supported by beveled surface 68 of support member 66. Flow restrictor 48, still fitted with screen 110 and O-ring 112, is engaged at threaded end section 74 to threaded surface portion 70 of tube container 52. Open inlet end 28 of testing tube 20 should be received within O-ring 112 to make a gas tight fit, thus preventing the refrigerant sample flow from bypassing testing tube 20. Flow restrictor 48 is then hand tightened to tube container 52. The time between breaking off frangible tips 24 and 26, completely assembling testing tube 20 in testing apparatus 50 and commencing the test should be minimized to reduce the possibility of false indications due to air contamination of the indicating media.

The test is commenced by again connecting hose line 56 to the system at suction line service valve 18 by means of Schraeder connector 58. For optimum oil removal efficiency, tube container 52, with testing tube 20 inserted, should be held so that its longitudinal axis is maintained vertical and end 28 is below end 30 throughout the test.

With the apparatus connected as described, the refrigerant sample, at system pressure, flows through hose line 56 into flow restrictor 48. Pressure reducing means 78 increases flow resistance and decreases sample flow rate thus reducing the pressure of the sample flow through pressure reducing means 78. This reduction in pressure is accomplished initially by collar section 82 and annular space 84, which reduce the area for the incoming flow. The sample flow continues through passage 92, which is reduced in cross section by continuously beveled surface 98, and orifice 96. The sample flow that passes through orifice 96 into passage 106 thus is reduced from system pressure to an acceptable pressure (near ambient) and flow rate. The reduced pressure flow then passes through opening 102 into testing tube 20 through inlet end 28 and out through outlet end 30.

Because of the rapid reduction in pressure of the refrigerant as it passes through orifice 96 into demister section 32, oil entrained in the sample will separate from the refrigerant and collect along the inner surface of demister section 32 as minute droplets. The sample flow and entrained contaminants then continue in the direction of arrow A through screen 36, disk 37, water removal and moisture indicating section 39, disk 40, screen 42, disk 43, acid indicating section 45, screen 46 and out outlet end 30.

After a prescribed testing time, ordinarily not more than ten minutes, Schraeder connector 58 is disconnected from suction line service valve 18 and testing tube 20 is immediately withdrawn from tube container 52. Any water or acid contaminants in the refrigerant vapor will be indicated by visible changes in the indicating media contained in indicator sections 39 and 45, respectively.

After test completion, hose line 56 and flow restrictor 48 is purged for subsequent tests. If hose line 56 and flow restrictor 48 are made of a disposable material, such as a suitable plastic, they can be discarded and replaced with a new hose line 56 and a new flow restrictor 48.

The acid indicating medium in acid indicator section 45 will change from blue to yellow in the presence of strong acids. The color change will extend through the medium from disk 43 in the direction of arrow A as a function of the acid concentration in the sample. The marks 45a can be used to determine the length of the color change. The length of the color change is then entered into Table I. For example, if the acid changes the bromophenol blue to yellow a distance equal to four markings 45a, then Table I is entered under the column designated marker No. at number 4 and then read across under the column indicating the testing time. If the flow was maintained for three minutes, then Table I would indicate an acid contamination of 0.20 parts per million. Similar tables can be empirically determined for water and other contaminants.

Table II illustrates another method of determining the amount or concentration of a contaminant, in this case water. Here the refrigerant sample is allowed to flow through testing tube 20 until the color of the indicating medium turns the same shade as that on a colored card (not shown). When the two colors match, the time required for the color change is entered into Table II. Should it take three minutes for the indicating medium to turn the same shade as on the colored card, then that would indicate a contamination level of approximately 270 parts per million.

TABLE I

| MARKER NUMBER | ACIDS APPROXIMATE PPM SAMPLING TIME | | | |
|---|---|---|---|---|
| | 1 MIN. | 3 MIN. | 5 MIN. | 10 MIN. |
| 1 | 0.2 | 0.06 | 0.04 | 0.02 |
| 2 | 0.3 | 0.10 | 0.06 | 0.03 |
| 3 | 0.4 | 0.13 | 0.08 | 0.04 |
| 4 | 0.5 | 0.20 | 0.11 | 0.05 |
| 5 | 0.6 | 0.21 | 0.13 | 0.06 |
| 6 | 0.8 | 0.26 | 0.15 | 0.08 |

TABLE II

| WATER VAPOR |
|---|
| 1 MINUTE INDICATES ABOUT 800 PPM |
| 3 MINUTES INDICATES ABOUT 270 PPM |
| 5 MINUTES INDICATES ABOUT 160 PPM |
| 10 MINUTES INDICATES ABOUT 80 PPM |

The procedure using other embodiments of the testing tube (FIGS. 3a through 3e) with additional indicating media for the indication of other refrigerant contaminants is similar to that described above except that, depending on tube configuration, tube holder 52 may not be used.

When a testing tube containing isolation membranes, e.g. membrane 341-1 (FIG. 3b), or capsules, e.g capsule 551 (FIG. 3d), is used, upon connection of hose line 56 to the system, pressure will build up in the testing tube upstream of the membrane or the upstream end of the capsule until the differential pressure across the membrane or capsule end is sufficient to break the membrane or capsule end. Then pressure will build up in the next section of the tube until the next membrane or capsule end is breached and so on until all membrane or capsule ends are breached and sample flow is established through the entire testing tube. This sequence is rapid and usually imperceptible to the ordinary observer.

In summary, to test a refrigeration, air conditioning or similar closed system for the presence of water or other contaminants using testing tube 20 (FIG. 3), a sample flow of refrigerant is taken from the system and passed at near atmospheric pressure into a testing tube. In the demister section of the tube any entrained oil is removed. The refrigerant and contaminants then pass through a screen and a disk into a water removal section. In this section, any water present is removed. This section may also be an indicator and produce a color change in an indicating medium whose distance of propagation through the medium is a measure of the water concentration. The removal of the water results in any remaining contaminants being present as anhydrous gases. The refrigerant and any remaining contaminants then pass through a disk, a screen and another disk before reaching an acid indicating section. The water and acid indicating sections are separated because the two indicating media could interreact causing false contaminant concentration indications. The acids react with the acid indicating medium producing a color change whose distance of propagation through the medium is a measure of the acid concentration. The presence and concentrations of other contaminants, i.e. volatile organic acids, carbon dioxide, carbon monoxide, hydrogen and oxygen may be determined by testing tubes containing suitable indicating media. The presence of excessive concentrations of excess water and other contaminants in the refrigerant indicates the need for replacing the refrigerant charge, adding conditioning agents to the refrigerant, or taking other corrective action. Detection of the presence of certain contaminants may also assist in assessing the condition of system components and in analyzing the cause of failures.

Although several preferred embodiments of the present invention have been described and illustrated, other embodiments may occur to one skilled in the art. For example, the present invention may be used not only for testing refrigeration, air conditioning and similar systems but for testing other types of systems as well. In addition, the specification discloses specific indicating media for indicating the presence of specific contaminants. Other suitable indicating media may be substituted for those disclosed. And one skilled in the art may develop other methods of fabricating the testing tubes described. It is therefore intended that the present invention be limited only by the scope of the below claims.

What is claimed is:

1. A method for testing a refrigerant for contaminants comprising the steps of:
    withdrawing a sample flow of said refrigerant from a closed system containing refrigerant;
    reducing the pressure of said sample flow;
    directing said flow to a testing tube containing contaminant indicating means;
    breaching isolation means within said testing tube to allow said flow to pass through said testing tube; and
    sequentially in said testing tube
    (a) removing any entrained oil from said sample flow,
    (b) removing water contamination from said sample flow, and
    (c) indicating the presence and concentration of at least one other contaminants in said sample flow.

2. The method of claim 1 in which the steps of withdrawing, pressure reducing and directing said refrigerant sample flow take place continuously throughout said testing.

3. The method of claim 2 in which said system is an operating refrigeration, air conditioning 4. The method of claim 1 in which said water contamination removal step includes the substep of indicating the presence and concentration of water contamination in said sample flow.

5. The method of claim 1 in which said indicating step comprises at least one of the substeps of indicating the presence and concentration of
    (a) inorganic acids,
    (b) volatile organic acids,
    (c) oxygen,
    (d) hydrogen,
    (e) carbon dioxide, and
    (f) carbon monoxide in said sample flow.

6. A means for testing for contaminants in a refrigerant contained in a system comprising:
    (a) a hollow tube,
    (b) means disposed within said hollow tube for separating entrained oil from a sample flow of said refrigerant from said system,
    (c) means disposed within said hollow tube for removing water contamination from said sample flow,
    (d) means disposed within said hollow tube for indicating the presence and concentration of at least one contaminant in said sample flow,
    (e) means disposed within said hollow tube for isolating said removing and said indicating means one from another and from the environment external to said hollow tube until the commencement of said testing, and
    (f) means for breaching said isolating means upon commencing said testing thus allowing said sample flow to come in contact with said removal and indicating means; and
    refrigerant pressure reducing and delivery means, in flow communication with said testing tube for directing said refrigerant flow at a reduced pressure from said system to said testing tube.

7. The testing means of claim 6 in which said testing means further comprises a tube container for holding and supporting said testing tube.

8. The testing means of claim 6 in which said water contamination removal means also indicates the presence and concentration of said water contamination in said sample flow.

9. The testing means of claim 6 in which said one or more other contaminant indicating means comprises means for indicating the presence and concentration of at least one of the following contaminants in said sample flow:
    (a) inorganic acids,
    (b) volatile organic acids,
    (c) oxygen,
    (d) hydrogen,
    (e) carbon dioxide, and
    (f) carbon monoxide.

10. The testing means of claim 6 in which said water contamination removal means further comprises water contamination presence and concentration indicating means and said testing tube includes means for viewing said water contamination removal and indicating means from outside said testing tube.

11. The testing means of claim 10 in which said water contamination indicating and removal medium is cobaltous chloride.

12. The testing means of claim 6 in which said contaminant indicating means indicate the presence and concentration of said contaminant and said testing tube includes means for viewing said indicating means from outside said testing tube.

13. The testing means of claim 12 in which said contaminant indicating media include at least one member of the group consisting of the following:
   (a) bromophenol blue in a glycerol film for indicating inorganic acids,
   (b) phenol red for indicating volatile organic acids,
   (c) titanium tetrachloride for indicating oxygen,
   (d) ammonium molybdate for indicating hydrogen,
   (e) hydrazine and crystal violet for indicating carbon dioxide, and
   (f) iodine pentoxide for indicating carbon monoxide.

14. The testing means of claim 6 in which said isolating means comprises a breachable film that is impervious to vapor and gas.

15. The testing means of claim 14 in which differential pressure across said breachable film breaches said breachable film, said differential pressure being created when said refrigerant enters said testing tube at the commencement of said testing.

16. The testing means of claim 6 in which said separating, removing and indicating means each comprise individual subsections that are assembled to form said testing tube.

17. The testing means of claim 6 in which said removal and indicating means each comprise individual cartridges that are inserted into said hollow tube to form, with said separating means, said testing tube.

18. The testing means of claim 6 in which said removal and indicating means each comprise individual capsules inserted into said hollow tube to form, with said separating means, said testing tube.

19. The testing means of claim 6 in which said testing means further comprises refrigerant flow indicator means in flow communication with said testing tube.

20. A means for testing for selected contaminants in a refrigerant contained in a system comprising:
   a testing tube comprising
   (a) a hollow tube,
   (b) a plurality of contaminant indicating means disposed within said hollow tube,
   (c) means disposed within said hollow tube for isolating said contaminant indicating means one from another and from the environment external to said hollow tube until the commencement of said testing and
   (d) means for breaching said isolation means upon commencing said testing thus allowing said refrigerant to come in contact with said contaminant indicating means; and
   a refrigerant pressure reducing and delivery means in flow communication with said testing tube for directing a flow of said refrigerant at a reduced pressure from said system to said testing tube.

21. The testing means of claim 20 in which said testing tube includes means for attaching said testing tube to said refrigerant pressure reducing and delivery means.

* * * * *